United States Patent [19]
Currier

[11] Patent Number: 5,897,514
[45] Date of Patent: Apr. 27, 1999

[54] RANGE OF MOTION LIMITER

[76] Inventor: Mark R. Currier, 85 St. James Ave., Milton, N.H. 03851

[21] Appl. No.: 09/020,450

[22] Filed: Feb. 9, 1998

[51] Int. Cl.[6] ........................................................ A61F 5/00
[52] U.S. Cl. ................................................ 602/16; 602/27
[58] Field of Search .................................. 602/5, 16, 20, 602/23, 26, 27–29; 128/882

[56] References Cited

U.S. PATENT DOCUMENTS 5,669,873   9/1997   Towsley ...................................... 602/26
5,672,152   9/1997   Mason et al. ............................... 602/26

Primary Examiner—Linda C. M. Dvorak
Attorney, Agent, or Firm—Mesmer Law Offices, P.A.; Brian C. Dauphin, Esq.

[57] ABSTRACT

An apparatus for quietly limiting motion at a limb joint having pivotally attached members for receiving the limbs of a joint and a dual-adjustable stop mechanism assembly attached to the members for restricting movement at the joint. The dual-adjustable stop mechanism assembly includes at least one bumper and a setscrew for adjusting the position of the bumper.

13 Claims, 6 Drawing Sheets

RANGE OF MOTION LIMITER

BACKGROUND OF THE INVENTION

1. Field of the Invention

The present invention relates generally to an orthopedic device for limiting limb motion. Particularly, this invention relates to an ankle-foot orthosis with a dual-adjustable stop system for quietly limiting the range of pivotal movement of the foot. Even more particularly, this invention relates to an ankle-foot orthosis with a single unit dual-adjustable stop system that allows for ease of manufacture. Still even more particularly, this invention relates to an ankle-foot orthosis with a dual-adjustable stop system that allows the angle of plantarflexion and dorsiflexion to be set and the pivotal movement of the foot permanently fixed.

2. Description of the Related Art

Hinged orthopedic braces having an adjustable range of pivotal movement, as disclosed by U.S. Pat. Nos. 5,022,390 (1991) and 5,328,444 (1994), both to Whiteside, are known in the art. The braces disclosed therein have adjustable stopping mechanisms to limit the range in pivotal movement of two hinged members of the brace relative to each other. The stopping mechanisms taught by the above-mentioned patents disclose an adjustable stop mechanism attached to one member of the brace and is positioned to come into contact with an abutment attached to the other member of the brace when the members are pivoted to a desired angle of restriction. As the wearer of a brace with this type of stopping mechanism takes a step, the stopping mechanism comes into contact with the abutment creating a loud clacking sound. This noise can be quite distracting or embarrassing to someone walking with the brace.

Other ankle-foot orthotic devices such as U.S. Pat. Nos. 5,399,152 (1995) to Habermeyer et al. and 5,429,588 (1995) to Young et al. disclose ankle foot orthoses designed to treat fractures and other injuries to the foot and ankle. Habermeyer discloses an apparatus that consists of two members pivotally connected. Each member provides surroundive fixation that is both removable and adjustable through the filling and evacuating of cushions within each member. Rear pivotal movement (plantarflexion) and front pivotal movement (dorsiflexion) are restricted by a bar with an attached abutment head contacting adjustable abutments located above and below the abutment head. One problem with this device is that the adjusting mechanism has multiple parts making it difficult and expensive to manufacture. Another problem with this device is that the parts are not easily replaceable by the wearer.

Young discloses an apparatus known in the art as a walker that consists of two members pivotally connected wherein plantarflexion and dorsiflexion are restricted between 22.5° of plantarflexion and 22.5° of dorsiflexion by adjustable screws contacting an upright side member. One problem with this device is that some wearers may require a greater range of motion than this device allows.

Still other foot and ankle devices such as U.S. Pat. Nos. 5,014,690 (1991) to Hepburn et al. and 5,144,943 (1992) to Luttrell et al. disclose dynamic splints which apply an adjustable force inducing either plantarflexion or dorsiflexion.

U.S. Pat. No. 5,044,360 (1991) to Janke discloses a foot ankle device with two members that are pivotally attached. Dorsiflexion and plantarflexion are restricted through the use of interchangeable cams, which have differing cam surfaces that come into contact with a rotatable stop. The unique shape of each interchangeable cam determines at what point or angle in plantarflexion or dorsiflexion the rotatable stop contacts the cam surface and limits range of motion.

U.S. Pat. No. 4,919,118 (1990) to Morris discloses a short leg walker which has a motion limiter consisting of a shaft pivotally attached to one of the walker's members and a sliding block pivotally attached to the remaining member. Restriction of plantarflexion and dorsiflexion occurs when the sliding block engages adjustable stop members, which are located above and below the sliding block. By adjusting the positions of the stop members, the range of motion can be limited accordingly.

There remains a need to provide a strong yet lightweight comfortable ankle-foot orthosis, which can effectively limit the ankle-joint against a wide range of pivotal movement and which is quiet in use. There also remains a need to provide a strong yet lightweight comfortable ankle-foot orthosis which has few parts and which is simple and inexpensive to manufacture. Additionally, there remains a need to provide a strong yet lightweight comfortable ankle-foot orthosis, which has dual-adjustable stop members that are easy to adjust and replace, which is concealable under clothing or footwear, and which is custom fit for the wearer. Still further, there remains a need to provide a strong yet lightweight comfortable ankle-foot orthosis that can set the angle of plantarflexion and dorsiflexion of the foot and that can permanently fix the pivotal movement of the foot.

SUMMARY OF THE INVENTION

It is therefore an object of the present invention to provide a comfortable ankle-foot orthosis that is strong and lightweight, which can effectively limit a wide range of plantarflexion of the ankle-joint and which is quiet in use. It is another object of the present invention to provide a comfortable ankle-foot orthosis that is strong and lightweight, which has few parts, and which is simple and inexpensive to manufacture. It is yet a further object of the present invention to provide a comfortable ankle-foot orthosis that is strong and lightweight, which has dual-adjustable stop members that are easy to adjust and replace, which is concealable under clothing or footwear, and which is custom fit for the wearer. It is yet a further object of the present invention to provide a comfortable ankle-foot orthosis that is strong and lightweight and that can set the angle of plantarflexion and dorsiflexion of the foot and that can permanently fix the pivotal movement of the foot.

The present invention achieves those and other objectives by providing a comfortable ankle-foot orthosis that is both strong and lightweight and that provides a single unit, multi-component, dual-adjustable stop system that allows for easy and inexpensive manufacture and that is quiet in use.

During manufacture the orthotic device is preferably formed of thermoplastic sheet material. This material is lightweight and can be shaped to intimately configure to a wearer's anatomy. Initially a single cast is made of the wearer's limbs. From this cast a male mold is made in configuration with the same shape of the wearer's limbs. Next, the stop system is attached as a single unit to the male mold using a self-adhesive spacer. Heated sheets of thermoplastic material are then superimposed over and vacuumed into intimate contact with the stop system and the male mold creating a single component system. After the thermoplastic material is sufficiently cooled the thermoformed single component system is sliced into two separate sections with each section having a portion of the stop system permanently attached. Hinges are then fastened on opposite sides of individual members of the orthotic device to allow for rotational movement of the individual members in relation to one another.

The single unit stop system, as it is attached to the male mold during manufacture, comprises a hollow tube that contains two independent impact bumpers. Inserts placed in each end of hollow tube prior to manufacture are fixed in position by the thermomolding process. The inserts are threaded for receiving setscrews. A setscrew is threaded through each insert and into an adjacent impact bumper prior to manufacture of the orthotic device. To add additional strength and stability to the stop system, an optional threaded spacer may be placed between an impact bumper and an insert.

After manufacture, the hollow tube is sliced through revealing the ends of the impact bumpers and creating exit holes in the hollow tube. Holes are then drilled through the thermoplastic material to reveal the ends of the setscrews. After the ends of the setscrews are revealed, a turning device is used to rotate each setscrew. As each setscrew rotates, it advances an impact bumper through a newly created exit hole. The further an impact bumper is advanced through an exit hole in the hollow tube the distance between the impact bumpers is reduced, thereby reducing the angle of permitted plantarflexion of the joint.

To set and restrict the angle of dorsiflexion and plantarflexion, the pair of impact bumpers and the setscrews may be removed and replaced with a threaded spacer and bolt. The threaded spacer is inserted into the hollow tube between the inserts. The bolt is then threaded through one insert, the threaded spacer and into the other insert. This eliminates the rotational movement of the thermomolded members. Different angles of dorsiflexion and plantarflexion may be established by varying the length of the threaded spacer.

DETAILED DESCRIPTION OF THE PREFERRED EMBODIMENT

Figure 1:
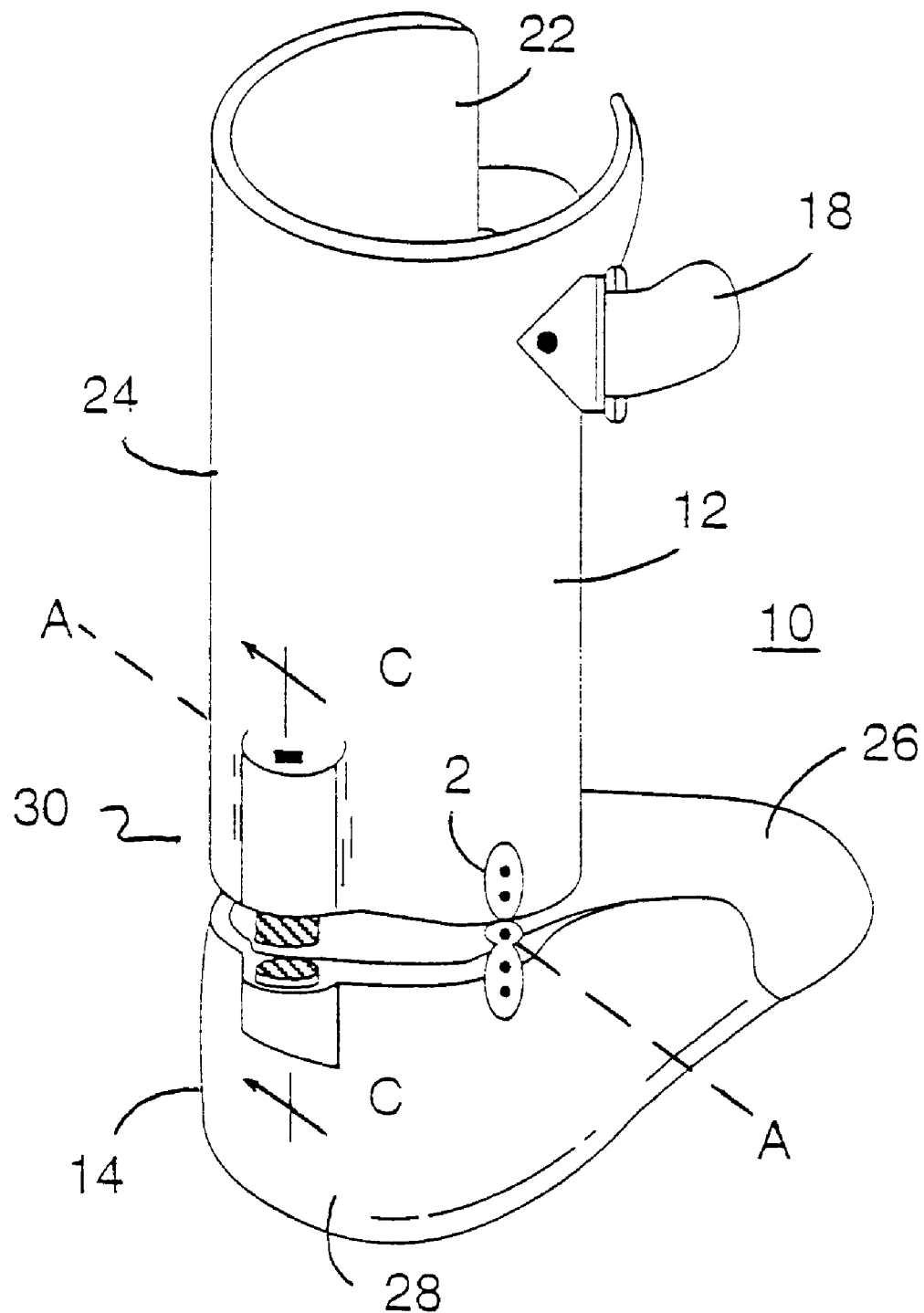
FIG. 1 is a perspective view of an orthotic device embodying the present invention.

A preferred embodiment of the present invention is illustrated in FIGS. 1–6. Referring now to FIG. 1 an ankle-foot orthotic device for limiting the motion of a foot about an ankle joint is designated by numeral 10. The present description is directed primarily to an ankle-foot orthotic device, however, the method of fabrication and use of orthotic device 10 can readily be applied to other joints of the human anatomy.

Orthotic device 10 has an ankle section 12 and a foot section 14, hingedly linked to rotate about an axis A—A, by hinge mechanisms 2 and 4. Orthotic device 10 is provided with a dual-adjustable stop system 30. Ankle section 12 has an inner surface 22 for accepting a wearer's lower leg and an outer surface 24. Ankle section 12 is shown provided with an adjustable strap 18 for securing the orthotic device to the wearer's lower leg. Adjustable strap 18 may employ a VELCRO, buckle, snap or other fastening system. Foot section 14 has both an inner surface 26 for receiving the wearer's heel and foot and an outer surface 28. An adjustable strap 20 (not shown) may be attached to foot section 14 for additional support in securing the orthotic device to the wearer's foot.

Figure 2:
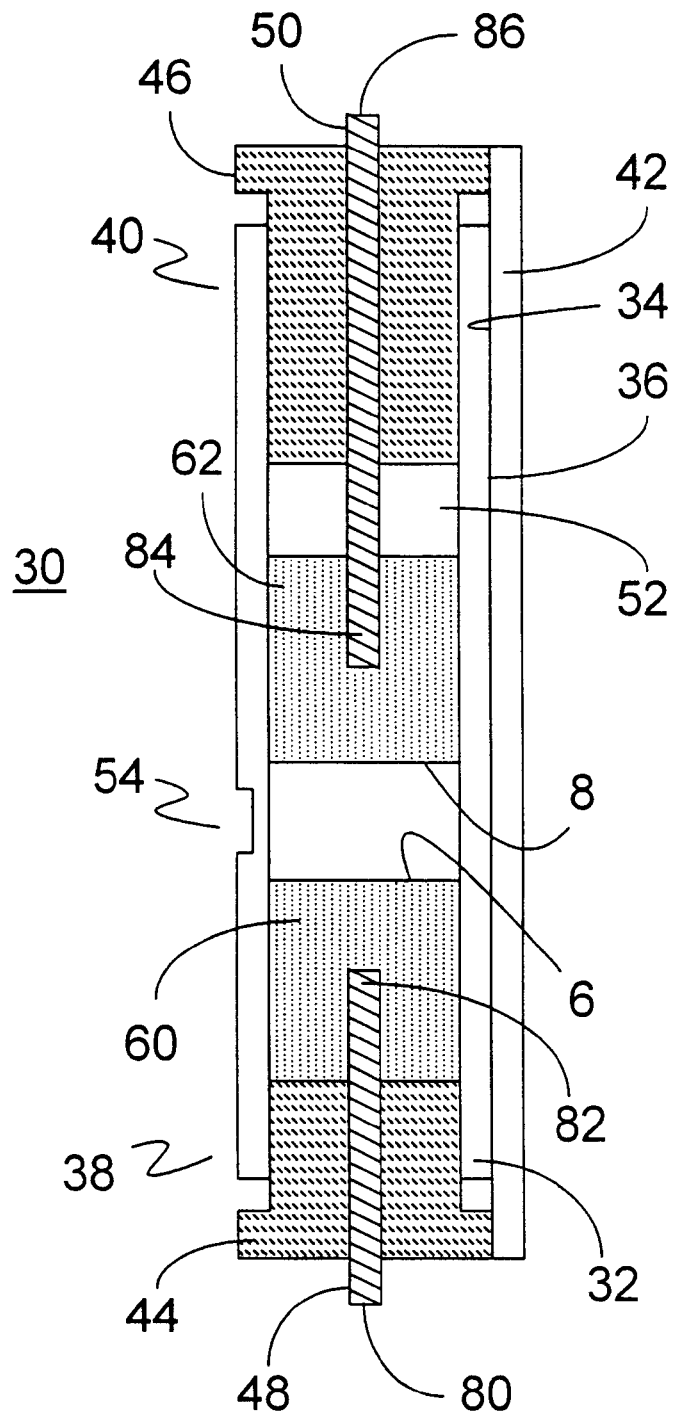
FIG. 2 is a cross-sectional view of the stop mechanism of the orthotic device, taken as indicated by the line C—C in FIG. 1.

FIG. 2 shows a cross-sectional view of the dual-adjustable stop system 30. Dual-adjustable stop system 30 has a hollow tube 32, having an inner surface 34, an outer surface 36, a first end 38, and a second end 40. A pair of impact bumpers 60 and 62, each slidingly engaged with the inner surface 34, are shown in first end 38 and second end 40 respectively. Impact bumpers 60 and 62, are made of a resilient material preferably a material such as polyurethane. At least one end of each impact bumper 60 and 62 contains a threaded recess. A pair of inserts 44 and 46 are also shown in first end 38 and second end 40 respectively, and are internally threaded.

An optional spacer 52 is shown inserted between impact bumper 62 and insert 46 and is also internally threaded. Optional spacer 52 provides additional rigidity to the dual-adjustable stop system 30. An additional optional spacer 52 may be included between insert 44 and impact bumper 60, or no spacers included at all. Setscrew 48, having first and second ends 80 and 82 respectively, is shown with end 82 threaded through insert 44 and partially into impact bumper 60. Setscrew 50, having first and second ends 84 and 86, is shown with end 84 threaded through insert 46, optional spacer 52 and partially into impact bumper 62.

Figure 3:
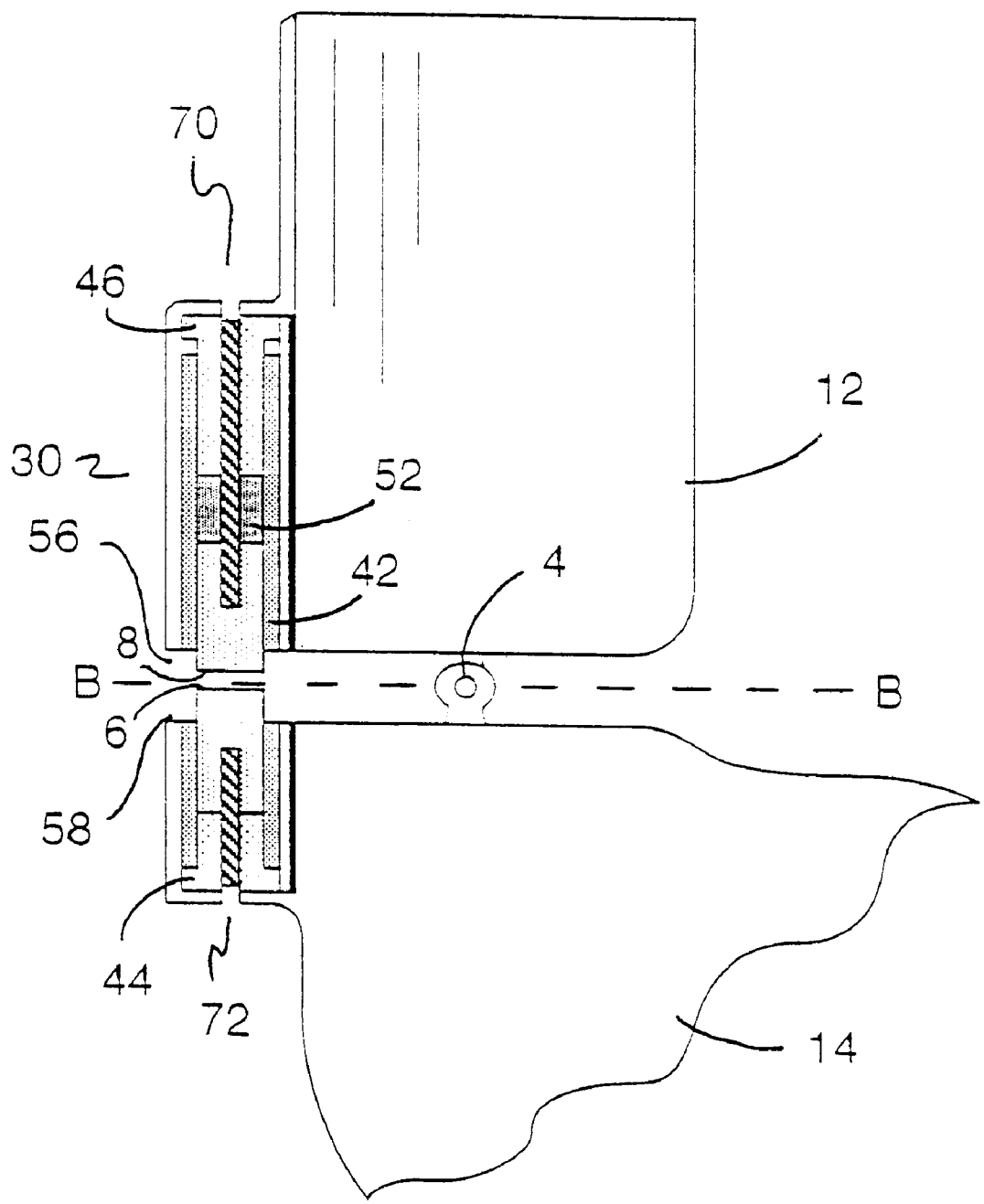
FIG. 3 is an enlarged, fragmentary, cross-sectional view of the orthotic device as shown in FIG. 1.

FIG. 3 shows orthotic device sections 12 and 14 linked by hinge mechanism 4, with a portion of the dual-adjustable stop system 30 thermoformed into each section. Insert 46 is shown having slightly larger dimensions than insert 44. This configuration lessens the interference between the orthotic device 10 and a wearer's shoe, but should not be considered limiting to the functionality of the device. Inserts 44 and 46 may be of equal proportions or insert 44 may be longer than insert 46.

Orthotic device sections 12 and 14 are preferably formed of thermoplastic sheet material. This material is lightweight and can be shaped to intimately configure to the wearer's anatomy. Initially a single cast is made of the wearer's limbs including the wearer's lower leg, ankle, heal and foot. From this cast a male mold is made in configuration with the same shape of the wearer's limbs. Next, the dual-adjustable stop system 30 is attached as a single unit to the heal portion of the male mold using a self adhesive foam spacer 42. Heated sheets of thermoplastic material are superimposed over and vacuumed into intimate contact with the dual-adjustable stop system 30 and the male mold. The dual-adjustable stop system 30 becomes permanently fixed in the thermoplastic material creating thermoformed assemblage 100 (not shown). After the thermoformed assemblage 100 is sufficiently cooled, it is sliced into two separate sections along cut line B—B. Slicing the thermoformed assemblage 100 into two parts creates exits holes 56 and 58 in hollow tube 32, reveals impact bumper ends 6 and 8 and creates orthotic device sections 12 and 14. Each orthotic device section retains a portion of the dual-adjustable stop system 30.

Hinge mechanisms 2 and 4 are fastened on opposite sides of orthotic device sections 12 and 14 using rivets, bolts, epoxy, or other fastening mechanism. Hinge mechanisms 2 and 4 may have moving parts like a door hinge or may be formed from a single piece of flexible material that will allow orthotic device sections 12 and 14 to pivot about axis A—A.

A notch 54 may be placed in outer surface 36 of hollow tube 32. Notch 54 represents a gap between impact bumpers 60 and 62 and indicates where to place the dual-adjustable stop system 30 on the male mold during the manufacturing process. Notch 54 is optional and may be placed on hollow tube 32 either prior to or subsequent to the installation of the impact bumpers 60 and 62, inserts 44 and 46 and optional spacer 52. If impact bumpers 60 and 62 are of equal size and inserts 44 and 46 are of equal size and optional spacer 52 is not utilized then notch 54 would be placed in the middle of the hollow tube 32. If impact bumpers 60 and 62 are different in size, inserts 44 and 46 are different in size or optional spacer 52 is used, then notch 54 will be offset from center. Preferably the hollow tube will be made of a translucent material which will ease in placing notch 54, as the space between the impact bumpers 60 and 62 will be seen through the hollow tube 32.

After bonding the dual-adjustable stop system 30 the device 10, holes 70 and 72 are drilled into the thermoplastic material to expose setscrew ends 86 and 80 respectively. Once exposed, setscrews 48 and 50 may be independently rotated to adjust impact bumpers 60 and 62 either forwards or backwards. As impact bumpers 60 and 62 are progressed together through exit holes 58 and 56 respectively the angle of allowable plantarflexion is reduced.

Figure 4:
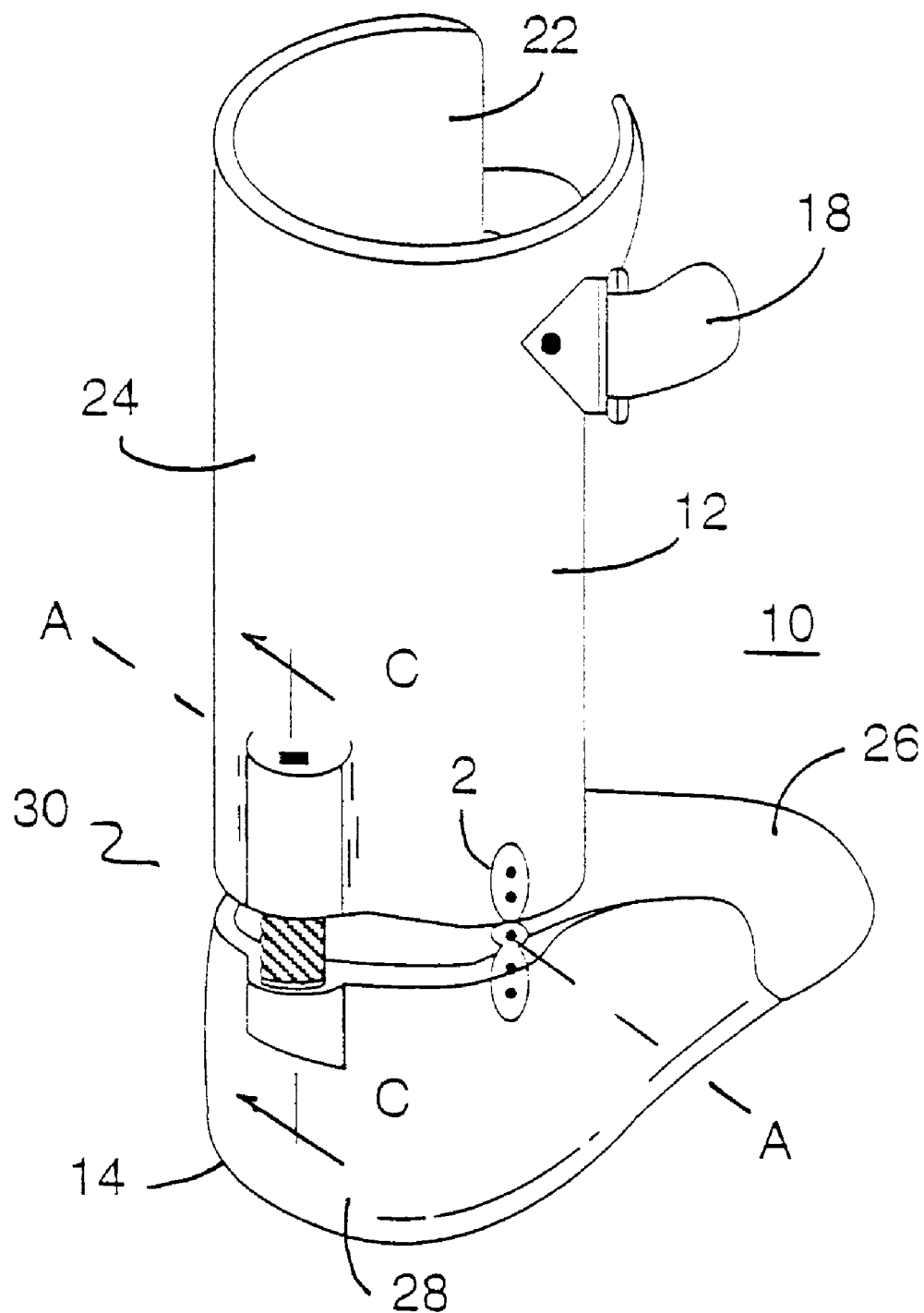
FIG. 4 is a perspective view of an orthotic device embodying the present invention.
Figure 5:
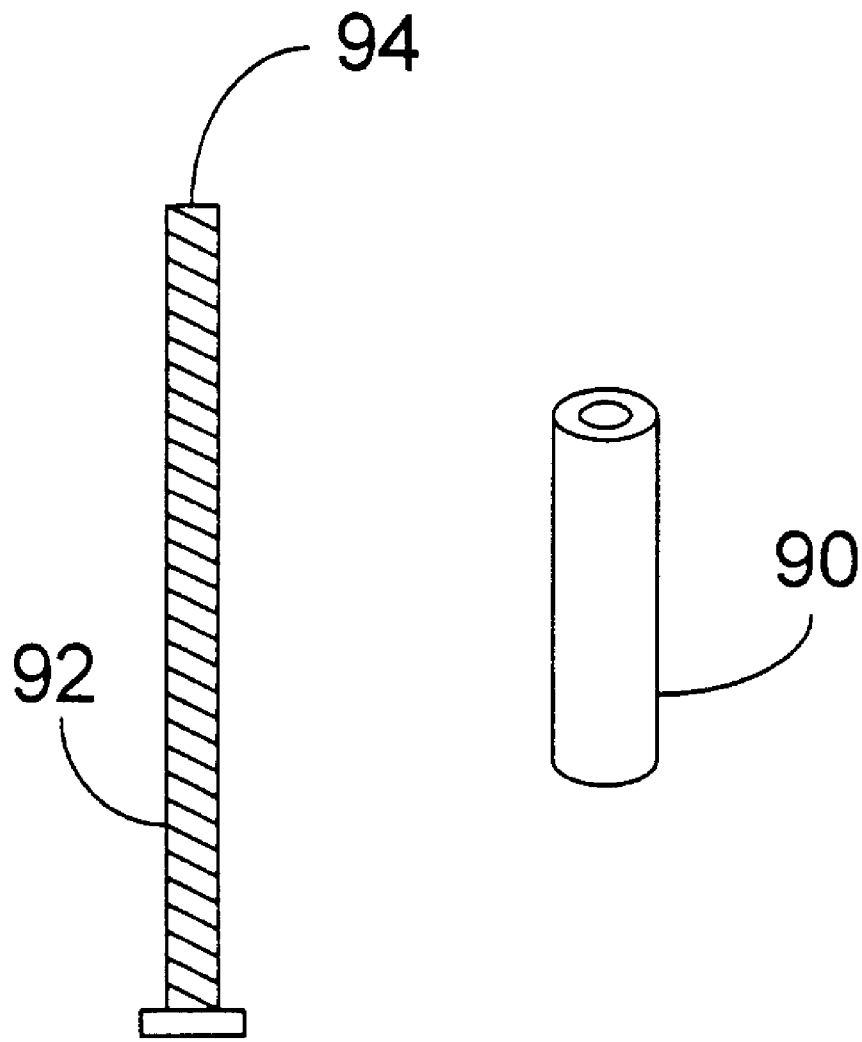
FIG. 5 is a perspective view of the threaded spacer and bolt as used with the stop mechanism of the orthotic device as shown in FIG. 4.
Figure 6:
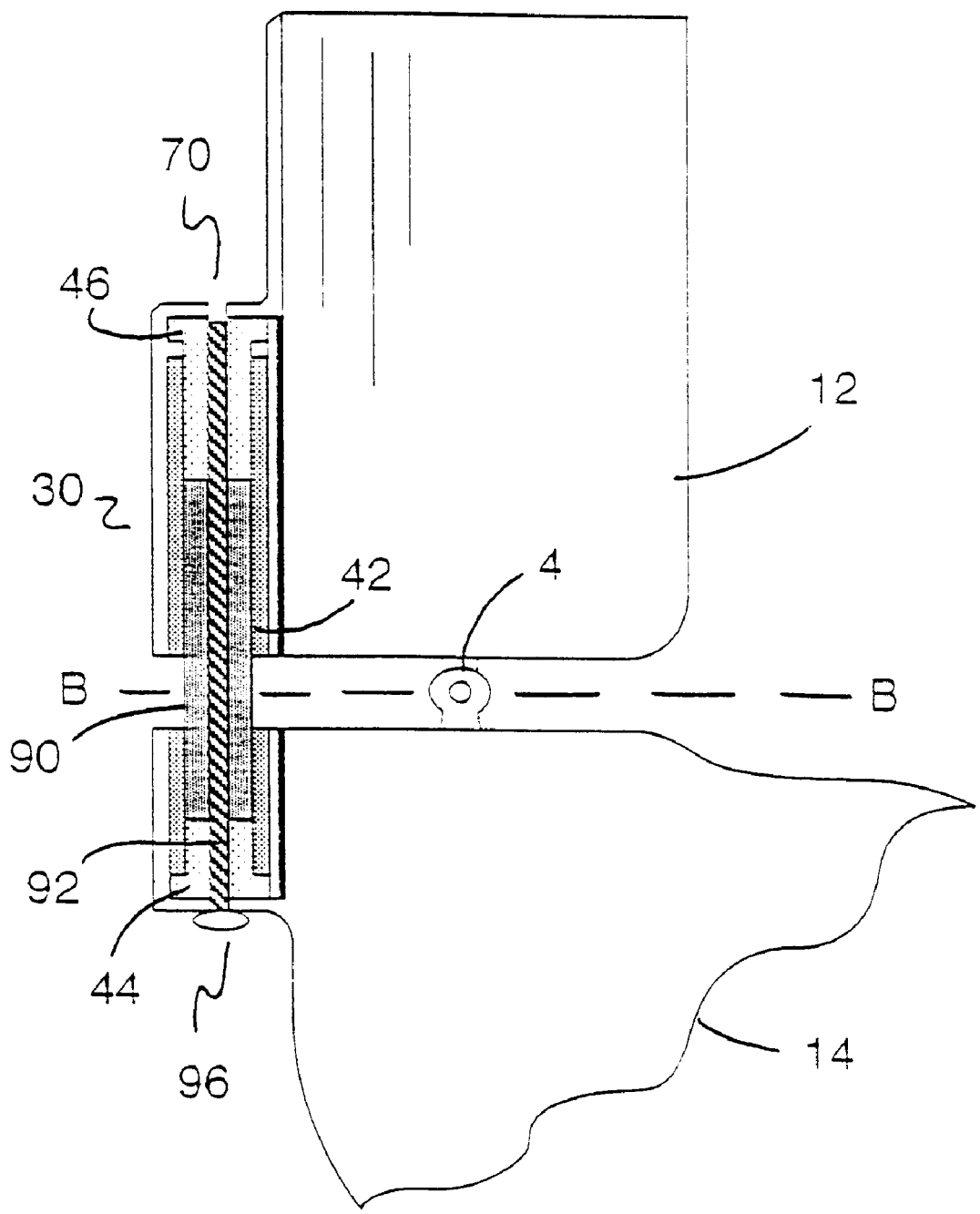
FIG. 6 is an enlarged, fragmentary, cross-sectional view of the orthotic device as shown in FIG. 4.

Referring now to FIGS. 4 through 6, a configuration for fixing the angle of orthotic device sections 12 and 14 with respect to each other and for completely restricting both dorsiflexion and plantarflexion is shown. Orthotic device sections 12 and 14 are shown as described above. Holes 70 and 72 are drilled into the thermoplastic material to expose setscrew ends 86 and 80 respectively. Setscrews 48 and 50 and impact bumpers 60 and 62 are removed from hollow tube 32. A threaded spacer 90 is inserted into ends 38 and 40 of hollow tube 32. A bolt 92 or other fastening means is then inserted through hole 72, through insert 44, through threaded spacer 90 and into insert 46. Bolt 92, which may also be inserted through hole 70, through insert 46, through threaded spacer 90 and into insert 44, prevents orthotic device sections 12 and 14 from rotating about axis A—A thereby preventing both dorsiflexion and plantarflexion. Setscrews 48 and 50 may also be used as the fastening mechanism for spacer 90. Setscrews 48 and 50 are inserted through holes 72 and 70, through inserts 44 and 46 and into opposite ends of threaded spacer 90, thereby securing orthotic device sections 12 and 14 to each other, and preventing both dorsiflexion and plantarflexion.

Although the preferred embodiment of the present invention has been described herein, the above descriptions are merely illustrative. Further modifications of the invention herein disclosed will occur to those skilled in the respective arts and all such modifications are deemed to be within the scope of the invention as defined by the appended claims.

What is claimed is:

1. An orthotic device for limiting motion in a limb joint comprising:
    (a) a first member;
    (b) a second member pivotally connected to said first member;
    (c) an adjustable stop mechanism comprising:
        1) a first adjustable range of motion limiter rigidly connected to said first member; and
        2) a second adjustable range of motion limiter rigidly connected to said second member, wherein said first adjustable range of motion limiter is axially aligned to impact said second adjustable range of motion limiter.

2. The orthotic device as claimed in claim 1, wherein said first range of motion limiter comprises:
    (a) a first internally threaded insert;
    (b) a first setscrew operatively threaded through said first internally threaded insert; and
    (c) a first impact bumper operatively connected to said first setscrew.

3. The orthotic device as claimed in claim 2, wherein said second range of motion limiter comprises:
    (a) a second internally threaded insert;
    (b) a second setscrew operatively threaded through said second internally threaded insert; and
    (c) a second impact bumper operatively connected to said second setscrew.

4. The orthotic device as claimed in claim 3, wherein said second impact bumper is fabricated from a resilient material.

5. The orthotic device as claimed in claim 4, wherein said resilient material is polyurethane.

6. The orthotic device as claimed in claim 2, wherein said first impact bumper is fabricated from a resilient material.

7. The orthotic device as claimed in claim 1, wherein said first range of motion limiter and said second range of motion limiter each comprises:
    (a) an internally threaded insert;
    (b) a setscrew operatively threaded through said internally threaded insert; and
    (c) an impact bumper operatively connected to said setscrew.

8. The orthotic device as claimed in claim 1, wherein said first adjustable range of motion limiter is operatively connected to said second adjustable range of motion limiter by an internally threaded spacer and at least one externally threaded fastener.

9. The orthotic device as claimed in claim 8, wherein said externally threaded fastener is a bolt.

10. The orthotic device as claimed in claim 8, wherein said externally threaded fastener is a combination of a first setscrew and a second setscrew.

11. A range of motion limiter for an orthotic device comprising:
    (a) a tube having an inner surface, an outer surface, a first end and a second end;
    (b) a first adjusting member comprising:
        1) a first internally threaded insert operatively located in said first end of said tube;
        2) a first screw mechanism threaded through said first internally threaded insert; and
        3) a first resilient material bumper operatively attached to said first screw mechanism and slidingly engaged with said inner surface of said tube;
    (c) a second adjusting member comprising:
        1) a second internally threaded insert operatively located in said second end of said tube;
        2) a second screw mechanism threaded through said second internally threaded insert; and
        3) a second resilient material bumper operatively attached to said second screw mechanism and slidingly engaged with said inner surface of said tube.

12. The range of motion limiter as claimed in claim 11, further comprising a threaded spacer operatively connected between said first resilient material bumper and said first threaded insert.

13. The range of motion limiter as claimed in claim 11, further comprising a threaded spacer operatively connected between said second resilient material bumper and said second threaded insert.

* * * * *